United States Patent [19]
Hundere et al.

[11] Patent Number: 5,337,599
[45] Date of Patent: * Aug. 16, 1994

[54] APPARATUS AND METHOD FOR DETERMINING THE THERMAL STABILITY OF FLUIDS

[75] Inventors: Alf Hundere; George R. Wilson, III; Thomas Dowda; James Dowda; David Anderson, all of San Antonio, Tex.

[73] Assignee: Alcor, Inc., San Antonio, Tex.

[*] Notice: The portion of the term of this patent subsequent to Apr. 7, 2009 has been disclaimed.

[21] Appl. No.: 863,856

[22] Filed: Apr. 6, 1992

Related U.S. Application Data

[63] Continuation of Ser. No. 711,120, Jun. 4, 1991, Pat. No. 5,101,658, which is a continuation of Ser. No. 618,117, Nov. 26, 1990, abandoned, which is a continuation of Ser. No. 511,646, Apr. 20, 1990, abandoned.

[51] Int. Cl.$^5$ ............................................. G01N 33/22
[52] U.S. Cl. ...................................... 73/61.62; 374/43
[58] Field of Search ........................... 73/61.62; 374/43

[56] References Cited

U.S. PATENT DOCUMENTS

| | | | |
|---|---|---|---|
| 3,670,561 | 6/1972 | Hundere | 73/61.62 |
| 4,176,544 | 12/1979 | Eyles et al. | 73/61.62 |
| 5,101,658 | 4/1992 | Wilson, III et al. | 73/61.62 |

FOREIGN PATENT DOCUMENTS

| | | | |
|---|---|---|---|
| 179084 | 2/1966 | U.S.S.R. | 73/61.62 |

Primary Examiner—Hezron E. Williams
Assistant Examiner—Joseph W. Roskos
Attorney, Agent, or Firm—Gunn, Lee & Miller

[57] ABSTRACT

An apparatus and method for determining the thermal stability of fluids, particularly for testing the deposition characteristics of fuels, comprising a conduit system which connects in series; a test fluid reservoir having a movable piston capable of discharging the fluid, a heater section in which is mounted a heated tubular member, a time reactor of a sufficient volume to increase the residence time of the fluid therein, and a water displacement reservoir. The system also incorporates a filter located at an outlet of the heater section designed to trap deposits which may form due to the heating, and a similar filter located at an outlet of the time reactor designed to trap further deposits that may form with additional time. A differential pressure measuring device is connected across each of these filters to measure the pressure drop therethrough. The apparatus also contains a water balanced reservoir and pressure regulator whereby the entire system may be maintained at a constant pressure and prevent the discharge of volatile fluids to the atmosphere.

16 Claims, 6 Drawing Sheets

APPARATUS AND METHOD FOR DETERMINING THE THERMAL STABILITY OF FLUIDS

This is a continuation-in-part of copending application Ser. No. 07/711,120 filed on Jun. 4, 1991 now U.S. Pat. No. 5,101,658, which is itself a continuation of U.S. patent application Ser No. 07/618,117, filed Nov. 26, 1990, which is a continuation of U.S. patent application Ser. No. 07/511,646, filed on Apr. 20, 1990, both abandoned.

BACKGROUND OF THE INVENTION

Field of the invention

This invention relates generally to methods and devices for measuring the thermal characteristics of fluids. Specifically, this invention relates to methods and devices for measuring the thermal oxidation tendencies of fluids, especially fuels, used in liquid hydrocarbon burning engines.

Description of the Related Art

All major liquid fuel burning engines potentially face the problem of restrictive deposits within their fuel systems that may result from poor fuel thermal oxidative stability. First seen as a problem for fuel systems utilized in gas turbine powered jet aircraft, the problems associated with fuel deposits have now become more widespread and down to earth with the increased use of port fuel injectors in automobile engines.

It was recognized early on that it would be necessary to have a test device that could rate the thermal oxidation characteristics of Jet fuels so that their deposit tendencies could be determined prior to use in aircraft. The standards for accomplishing this test have for many years been defined by ASTM method D-3241 which utilizes an apparatus based upon U.S. Pat. No. 3,670,561 (Hundere patent). The present application is an improvement upon the Hundere patent, utilizes its basic design as a starting point, and additionally provides a means for retrofitting the original Hundere device with the various improvements disclosed herein.

The earlier Hundere patent was designed specifically for testing the deposit characteristics of jet fuels and comprised a single reservoir containing fresh and tested fuels on opposites sides of a movable piston, in combination with a single heated test vessel, all within a closed test loop. In the Hundere patent fresh fuel was supplied to the test vessel within which a heated tubular member exposed the fuel to a known temperature for a selected period of time. A return line from this heated vessel went through both a cooling system and a constant speed metering pump which maintained the fuel flow within the system and returned the tested fuel to the fuel reservoir. A filter designed to trap deposits which remained suspended in the fuel due to the heating, was located at the outlet of the heated vessel, and a differential pressure measuring device was connected across the filter to measure the pressure drop therethrough. By examining this filter and the heated tubular member for solid deposits, the thermal stability of the fuel could be determined. The earlier Hundere apparatus also utilized a pressurized inert gas source whereby the entire system could be kept at a constant pressure in order to help maintain an accurate flow through the heated test vessel and to prevent the heated test fuel from boiling.

While the apparatus of the Hundere patent has provided a quality standard for testing jet fuel and has been widely used in the industry, the increased demand for higher tech fuels and the use of engines with finer fuel tolerances have disclosed some drawbacks and deficiencies in the original Hundere design. In general, there are five areas of difficulty experienced by the original design that have developed as demands upon the testing apparatus have evolved.

A first difficulty involves the ability to identify deposits that require high residence times in a heated condition for their formation. Evidence of this problem could be seen in both the original apparatus itself and in the real world of aircraft and automobile engines. In the real world, changes in the design of engines have created an environment whereby fuels come in contact with heated surfaces for periods of time longer than the Hundere patent was designed to test. Within the apparatus itself, the problem is evidenced by the retention of solids within the metering pump mechanism and other downstream components which formed only after high resident time periods. These solids appear outside those parts of the apparatus where quantitative measurements are normally made.

A second difficulty derives from the method of pumping the test fuel through the test apparatus. In the Hundere patent the circulation of the fuel was controlled by an in-line metering pump and was to some extent influenced by the constant pressure on the system supplied by the inert gas source. Because the system pump was in-line the fuel flow rate was in part determined by the viscosity of the fuel and in part by the efficiency of the pump. Because the pump was susceptible to both wear and contamination from suspended solids in the heated fuel, the flow rate could vary as much as 20% depending upon the age of the pump or the extent to which it had become clogged with deposits.

A third difficulty with the Hundere patent involves the above mentioned necessity of maintaining the test fuel under the constant pressure of an inert gas source. Apart from the inconvenience of the ancillary components needed to provide the constant background pressure, the system required a mechanism for cutting the pressure when a fuel leak occurred. A preferable alternative would be a system that did not require the constant auxiliary background pressure of the Hundere patent and in general could execute the test under conditions that would allow only small amounts of fuel to escape in the event of a leak.

A fourth difficulty, which is related in some respects to the first difficulty associated with the need for increased residence time, has to do with the inability of the original apparatus to obtain quantitative (or qualitative) measurements of the additional deposits which formed downstream from the heater section. Not only did these downstream deposits cause problems for the in-line pump, but it was not possible to measure them and consider them in the fuel quality analysis.

A final difficulty involves the overall operation of the previous Hundere design, and the necessity of the constant attention of a test operator. While if properly done, a test utilizing the original Hundere apparatus could provide quite accurate results, there were many opportunities for faulty tests to occur due to the failure of the test operator to properly attend to the steps in the process. Some type of automated system, at least for some of the steps involved in the process, would certainly be preferable to the constant attention required by the earlier designs.

Altogether, these various difficulties, while they are not fatal to the functionality of the original Hundere device, leave open a number of areas where various improvements would greatly increase the efficiency of a test apparatus designed to determine the deposit characteristics of jet fuels and the like. It is in the above mentioned five areas of difficulty that the present invention seeks to improve upon the prior methods of testing fluids and fuels for their thermal oxidation characteristics.

SUMMARY OF THE INVENTION

It is therefore an object of the present invention to provide an apparatus and method for the testing of fluids.

It is another object of the present invention to provide an apparatus and method for testing the thermal oxidation characteristics of fluids.

It is another object of the present invention to provide an apparatus and method for measuring the tendency of fluids, particularly fuels, to form deposits when in contact with heated surfaces.

It is another object of the present invention to provide an apparatus and method for testing the thermal oxidation tendencies of fluids, particularly fuels, which apparatus and method utilize a relatively small test sample, and which involve a relatively simple sequence of steps for operation.

It is another object of the present invention to provide an apparatus and method for testing the thermal oxidation tendencies of fluids, particularly fuels, which apparatus and method provide multiple points at which quantitative measurements may be taken of deposits that form within the test fluid as a result of thermal oxidation.

It is another object of the present invention to provide an apparatus and method for testing the thermal oxidation tendencies of fluids, particularly fuels, which apparatus and method are capable of testing a broad range of fuels including jet fuels, automobile gasolines, and diesel fuels.

It is another object of the present invention to provide an apparatus and method for testing the thermal oxidation tendencies of fluids, particularly fuels, which apparatus and method can accurately determine thermal oxidation tendencies over extended periods of time and thereby facilitate a more accurate prediction of the quality of the fluid and its ability to function under conditions of prolonged heating.

It is another object of the present invention to provide an apparatus and method for testing the thermal oxidation tendencies of fluids, particularly fuels, which apparatus and method can accurately control and take into account small variations in the flow rate of the fluid being tested, so as to be capable of distinguishing the effect of flow rate on the deposition rate of the fluid.

It is another object of the present invention to provide an apparatus and method for testing the thermal oxidation tendencies of fluids, particularly fuels, which apparatus and method utilize an open ended flow system, and eliminate the requirement of a circulating test fluid pump that would have the tendency to become clogged with fluid deposits.

It is another object of the present invention to provide an apparatus and method for testing the thermal oxidation tendencies of fluids, particularly fuels, which apparatus and method employ means for maintaining a pressurized test fluid, but which eliminate the potential energy spring problems associated with pneumatically pressurized systems, and still maintain a system that inhibits test fluid vaporization.

It is another object of the present invention to provide an apparatus and method for testing the thermal oxidation tendencies of fluids, particularly fuels, which apparatus and method control many of the steps in the test process with an automatic system that reduces the necessity of operator intervention.

In fulfillment of these and other objects, the present invention provides an apparatus and method for determining the thermal stability of fluids and in particular for testing the deposition characteristics of fuels comprising a conduit system which connects in series, a test fluid reservoir having a moveable piston therein capable of forcing the test fluid through the test system, a heater section within which is mounted a heated tubular member, that raises the test fluid temperature to a level at which oxidation reactions may occur, a time reactor of a sufficient volume to increase the residence time of the heated fluid therein, thereby increasing the amount of deposits which may be collected that form as a result of the oxidation reactions, and a water displacement reservoir, which receives the tested fluid and displaces out of the system equal amounts of water as a non-volatile, non-toxic effluent. The system also incorporates a series of filters located at the outlet of the heater section and of the time reactor, which are designed to trap deposits that form due to the oxidation reactions within the test fluids. A differential pressure measuring system is connected across each of the filters, so as to measure the pressure drop therethrough, and to acquire an indirect quantitative measure of the degree of deposit buildup on each filter. The apparatus additionally contains a pressure regulator, whereby the entire system may be maintained at a constant pressure in a manner that improves the control of the flow rate, and prevents the vaporization of the test fluid during heating. The entire system is controlled by a solid state system controller and data acquisition device, which not only initiates and terminates the steps of the process when appropriate, but acquires quantitative data from the system on a real time basis. Other objects of the present invention will become apparent to those skilled in the art from the drawings and descriptions given herein and in the appended claims.

DESCRIPTION OF THE PREFERRED EMBODIMENT

Figure 1:
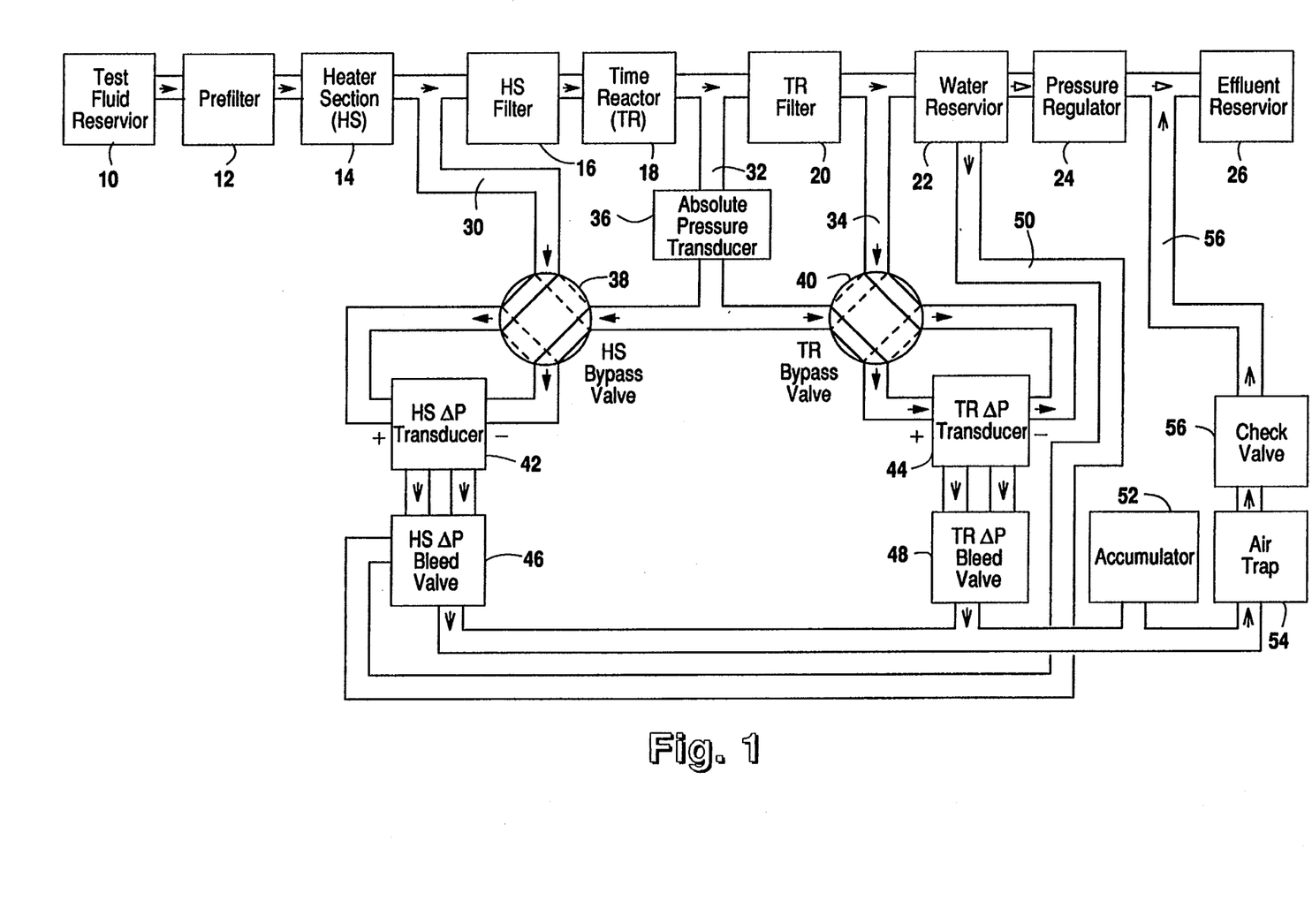
FIG. 1 is a schematic block diagram of the fluid flow arrangement of the apparatus of the preferred embodiment of the present invention.

Reference is first made to FIG. 1 for a detailed description of a schematic block diagram showing the essential components of the apparatus of the preferred embodiment of the present invention, the flow of the test fluid and other fluids between the various components, and the conduction of various pressures from one point to another in the system.

There are essentially four sub-systems within the test apparatus shown in FIG. 1. The first sub-system is the test fluid flow system, and includes test fluid reservoir 10, prefilter 12, heater section 14, heater section filter assembly 16, time reactor 18, time reactor filter assembly and terminates with water reservoir 22.

A water displacement sub-system includes water reservoir 22, pressure regulator 24, and effluent reservoir 26. A pressure measurement sub-system includes absolute pressure transducer 36, heater section bypass valve 38, time reactor bypass valve 40, heater section differential pressure transducer 42, and time reactor differential transducer 44. A fourth and final sub-system is the bleed/vent system, and includes heater section pressure bleed valve 46, time reactor pressure bleed valve 48, accumulator 52, air trap 54, check valve 56, and finally effluent reservoir 26. Each of these sub-systems will be described in more detail below.

The primary test fluid flow system of the preferred embodiment of the present invention carries a flow of test fluid from an initial reservoir through to a final reservoir. Test fluid begins at test fluid reservoir 10, and is forced from test fluid reservoir 10 by means described in more detail below. The test fluid is initially clarified by prefilter 12 before it is forced into heater section 14. The flow of the test fluid through heater section 14 terminates through heater section filter assembly 16. Once the test fluid has been raised to a predetermined high temperature, thermal oxidation begins to occur, and deposits within the fluid begin to appear. These deposits are filtered by heater section filter assembly 16, and the test fluid is allowed to pass on into time reactor 18. In a manner similar to heater section 14, time reactor 18 terminates with time reactor filter assembly 20. Time reactor 18 allows for an increased residence time for the heated test fluid to continue to react and deposit out impurities. After passing through time reactor 18, the test fluid is conducted into water reservoir 22 where it displaces a volume of water previously placed within water reservoir 22. The test fluid is captured and retained until such time as the test is complete and the test operator opens water reservoir 22 to remove the spent test fluid.

The water displacement sub-system, which includes water reservoir 22, pressure regulator 24, and effluent reservoir 26, is simply an extension of the test fluid flow system described above. The water displacement system allows for a controlled back pressure on the entire test fluid system without the necessity of exposing the spent test fluid to the atmosphere, nor the necessity of having to adjust pressure regulator 24 to varying test fluid viscosities and impurities.

As described above, test fluid from time reactor 18 enters water reservoir 22 and displaces an equal amount of water out of water reservoir 22 by way of pressure regulator 24. Pressure regulator 24 is adjustable so as to maintain a constant back pressure on the system, and to indirectly control the flow rate of the test fluid through the test fluid system. This flow rate helps to determine the residence time, both in heater section 14, and in time reactor 18. After passing through pressure regulator 24, the displaced water from water reservoir 22 passes into effluent reservoir 36, which is simply an open container of a-sufficient volume to capture the effluent water.

Of critical analytical importance to the system is the ability of the apparatus to determine deposit buildup across heater section filter assembly 16 and time reactor filter assembly 20. Since these filter assemblies are in line with one another, there are only three points that need to be tested in order to determine a differential pressure across each filter. A first pressure value is obtained between heater section 14 itself and heater section filter assembly 16, which pressure value is compared with a pressure value on the opposite side of heater section filter assembly 16. Likewise, a pressure value is obtained prior to time reactor filter assembly 20, and after time reactor filter assembly 20.

The pressure measurement sub-system is made up primarily of differential pressure transducers 42 and 44, which measure the differential pressure across the above mentioned filters. This pressure measurement sub-system additionally includes absolute pressure transducer 36, which determines an absolute pressure within the system for both quantitative measurement concerns and for safety concerns. The pressure points described above are communicated to differential pressure transducers 44 and 42 by way of bypass valves 38 and 40, which when appropriate, may allow the test fluid to pass from heater section 14 directly into water reservoir 22, without passing through either of filter assemblies 16 or 20. In the standard test configuration, however, bypass valves 38 and 40 are configured to simply communicate the pressure found at the points mentioned above to differential pressure transducers 44 and 42.

A first pressure point (+P1) between heater section 14 and heater section filter assembly 16 is conducted to the positive side of heater section differential pressure transducer 42, and a second pressure point (−P1) is conducted through absolute pressure transducer 36 from time reactor 18 by way of heater section bypass valve 38 through to the negative side of differential pressure transducer 42. This then gives the differential pressure value across heater section filter assembly 16.

A similar arrangement is configured for time reactor filter assembly 20. What was the second (lower) pressure value for heater section filter assembly 16 is utilized as the first (higher) pressure value (+P2) for time reactor filter assembly 20. This same pressure point is conducted through absolute pressure transducer 36, through time reactor bypass valve 40 to the positive side of time reactor differential pressure transducer 44. The negative value (−P2) of the differential pressure is obtained after time reactor filter 20, and is conducted to differential pressure transducer 44 by way of bypass valve 40. This gives a differential pressure value measured by differential pressure transducer 44, which is indicative of deposit build up across time reactor filter assembly 20.

If it is desirable to bypass filter assemblies 16 and 20 altogether, then bypass valves 38 and 40 may be rotated so as to redirect the flow of the test fluid from heater section 14 into bypass valve 38, and then directly to bypass valve 40. From bypass valve 40 the test fluid flow is directed back into the system at water reservoir 22. This "removes" filter assemblies 16 and 20 and time reactor 18 from the flow system. This might be necessary if heater section filter assembly and/or time reactor filter assembly 20 received deposits in excess of their capacity or if the system is started empty and it is necessary to eliminate air from the system. Thus, this bypass system serves both a safety function, and a system restart function.

Finally with reference to FIG. 1, there is an ancillary bleed/vent system that allows the reset of the pressures in differential pressure transducers 44 and 42, and the venting of any pressurized vapors present in water reservoir 22. The bleed/vent system comprises heater section pressure bleed valve 46 and time reactor pressure bleed valve 48, which allow an outlet for the pressurized fluids conducted to heater section differential pressure transducer 42 and time reactor differential pressure transducer 44. Once a test has been run, these pressures must be released to reset the system. This release is accomplished by way of bleed valves 46 and 48. Each of these valves 46 and 48 conducts released pressurized fluid through accumulator 52, air trap 54, check valve 56, and finally into effluent reservoir 26. In addition to the release of pressure from differential pressure transducers 44 and 42, the bleed/vent system allows for the venting of vapors from water reservoir 22, which may be present when the test fluid enters water reservoir 22. This venting is accomplished by way of heater section differential pressure bleed valve 46, and the same series of components; accumulator 52, air trap 54, check valve 56, and finally, effluent reservoir 26. As with the bypass system described above in connection with the differential pressure measuring sub-system, the bleed/vent system is utilized both for safety, and for resetting the system for a new test.

Figure 2:
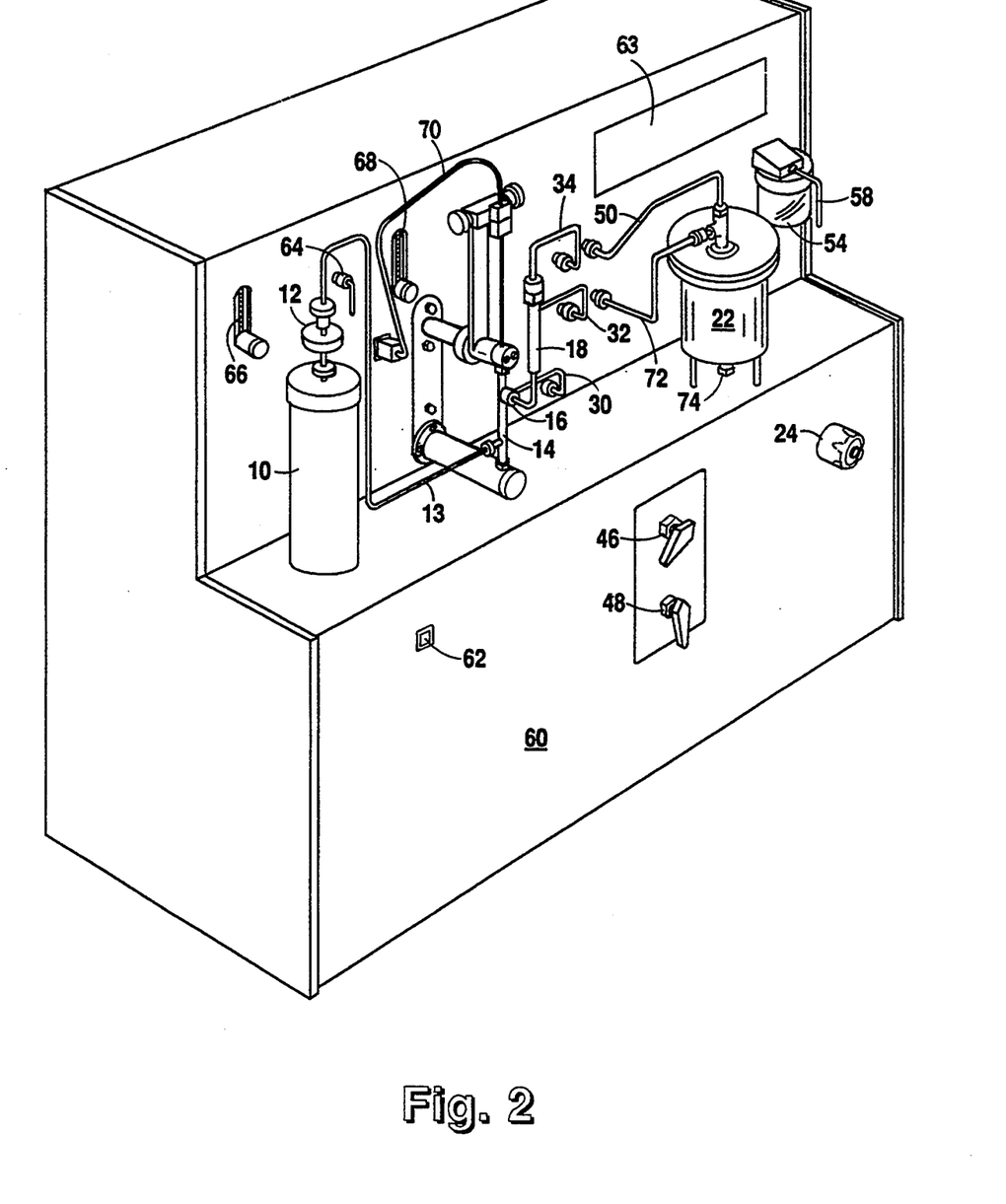
FIG. 2 is a perspective view of the front of a typical arrangement of the apparatus of the preferred embodiment of the present invention.

Reference is now made to FIG. 2 for a detailed description of the front panel configuration of a typical arrangement of the apparatus of the preferred embodiment of the present invention. The apparatus may be configured in a cabinet with many of the components that require no operator access concealed behind the cabinet walls, and with the balance of the components that require some operator access appropriately placed outside of the cabinet in the sequence of the test flow system.

In FIG. 2, the front of test system cabinet 60 is disclosed showing the components of the system which require operator access. Power switch 62 is activated to power up the system and to initiate a sequence of command steps which are displayed on display 63 and which are interactively controllable by the test operator.

Initially, the test fluid to be utilized is aerated with air from aeration port 64. This aeration is controlled and regulated by aeration flow control 66. This aeration is essential for the proper testing of the test fluid, because it introduces into the fluid an appropriate amount of oxygen and other gases that allow oxidation reactions to occur, which in turn allows deposits to form within the fluid and precipitate out of the liquid state.

Once the test fluid has been aerated, it is placed within test fluid reservoir 10 and is sealed inside. The test sequence is then initiated, and test fluid is forced from test fluid reservoir 10, through prefilter 12, and through test fluid conduit 13. Test fluid conduit 13 conducts the test fluid to heater section 14 where it is raised to a predetermined temperature, and the oxidation reactions are initiated. The temperature of the test fluid within heater section 14 is monitored by thermocouple assembly 70. Heater section 14 is heated by means described in more detail below, and its electrical connections and components are cooled by a liquid coolant system. This liquid coolant flow is controlled and monitored by way of liquid coolant flow control 68. From heater section 14, the test fluid is conducted into time reactor 18. A first differential pressure measurement is obtained by way of first differential pressure port 30. A second differential pressure measurement is taken at second differential pressure port 32. After leaving time reactor 18, a third differential pressure measurement is taken at third differential pressure port 34.

From time reactor 18, the test fluid is directed into water reservoir 22 by way of spent fluid conduit 72. Also attached to water reservoir 22 is vent conduit 50, which draws away any vapors which may collect within water reservoir 22. The test fluid displaces water already present in water reservoir 22, and forces the water out through water conduit 74. Water from water reservoir 22 passes through pressure regulator 24, which provides a constant back pressure on the entire system during its operation. From pressure regulator 24, water from water reservoir 22 passes into effluent reservoir 26 (not shown) by way of air trap 54 and effluent conduit 58.

Additionally shown, but not normally altered in the operation of a standard test are heater section bleed valve 46 and time reactor bleed valve 48. These valves allow the system to be bled and reset once a test has been run. Their operation is described in more detail above in relation to a description of FIG. 1.

Figure 3:
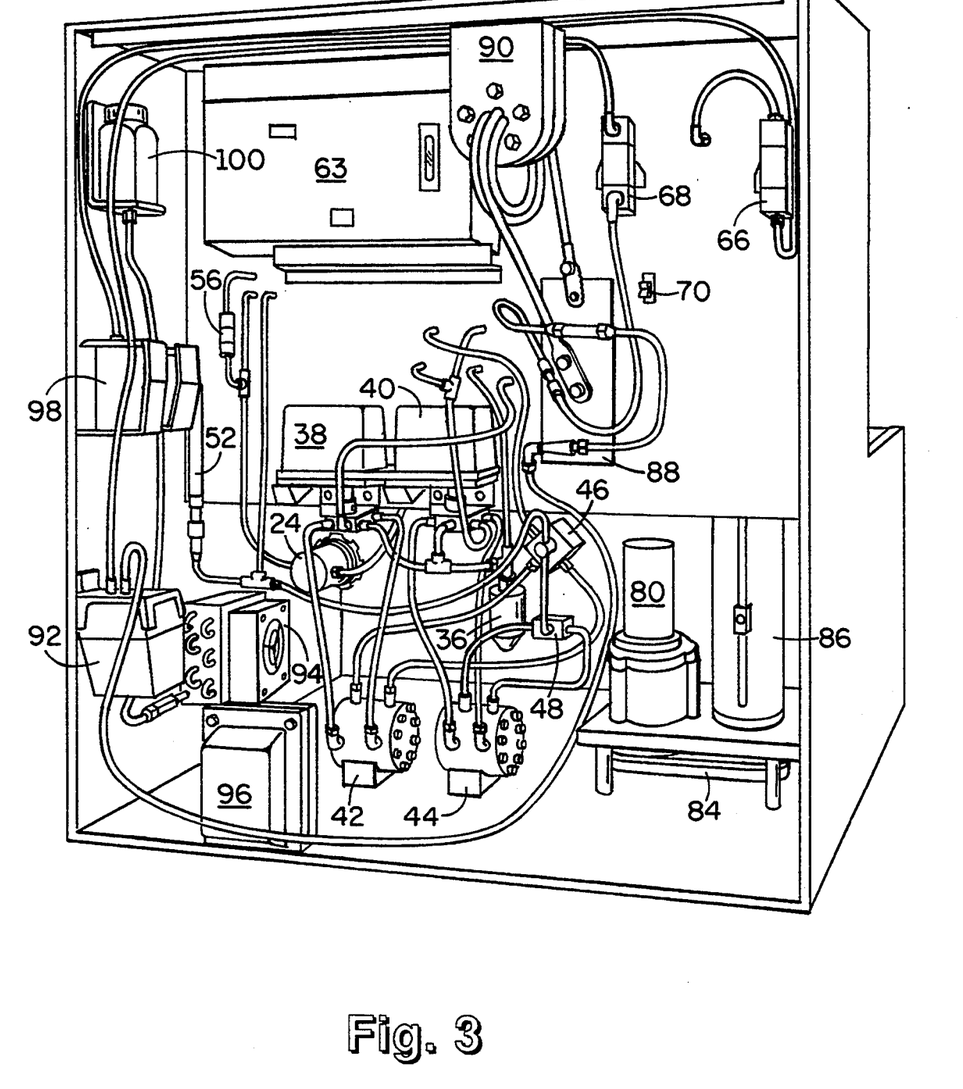
FIG. 3 is a perspective view of the back of the apparatus of the preferred embodiment of the present invention shown in FIG. 2.

Reference is now made to FIG. 3 for a detailed description of the components present within cabinet 60, shown in FIG. 2, but with the components of the system previously concealed now disclosed. In FIG. 3, aeration flow control 66 is shown in its position behind the front wall of cabinet 60. Adjacent aeration flow control 66 is coolant liquid flow control 68. Below test fluid reservoir 10 (not shown in FIG. 3) is positioned drive motor 80, gear reducer 82, drive belt 84, and drive screw 86. Together these components direct a piston (not shown) up into test fluid reservoir 10 so as to force the test fluid from reservoir 10 into the system. Drive motor 80 and the various components associated with it are controlled by the automated electronics of the system and are described in more detail below with respect to FIG. 7.

Heating assembly 88, which provides the necessary heating and cooling elements to heater section 14, is shown in general in FIG. 3, but is described in more detail below with respect to a description of FIG. 4. Shown associated with heating assembly 88 is electrical heater transformer 90.

Bypass valves 38 and 40 direct the flow of the pressurized test fluid for the purpose of determining differential pressures during the normal operation of the test apparatus, and when appropriate, redirect the flow of the test fluid around the filters in the manner described above with respect to FIG. 1. Associated with these bypass valves 38 and 40 is absolute pressure transducer 36. The primary components of the differential pressure measurement system are heater section differential pressure transducer 42, and time reactor differential pressure transducer 44.

Connecting the differential pressure measuring system to the bleed/vent system are heater section pressure bleed valve 46, and time reactor pressure bleed valve 48. Bleed valves 46 and 48 are shown attached to the front of cabinet 60, whereby their controls extend through the front wall of the cabinet to be regulated by the test operator.

Most of the flow of the test fluid through the system occurs outside of the cabinet, and is described with regard to FIG. 2 above. This flow of test fluid displaces an amount of water in water reservoir 22 (FIG. 2), which displaced water passes into cabinet 60 before it passes back out to the front of cabinet 60 and into effluent reservoir 26 (not shown).

Ancillary components, which are also disclosed in this rear view of cabinet 60 shown in FIG. 3, include coolant liquid pump 92, coolant coil and fan assembly 94, system power transformer 96, aeration pump 98, water supply reservoir 100, and accumulator 52.

Figure 4:
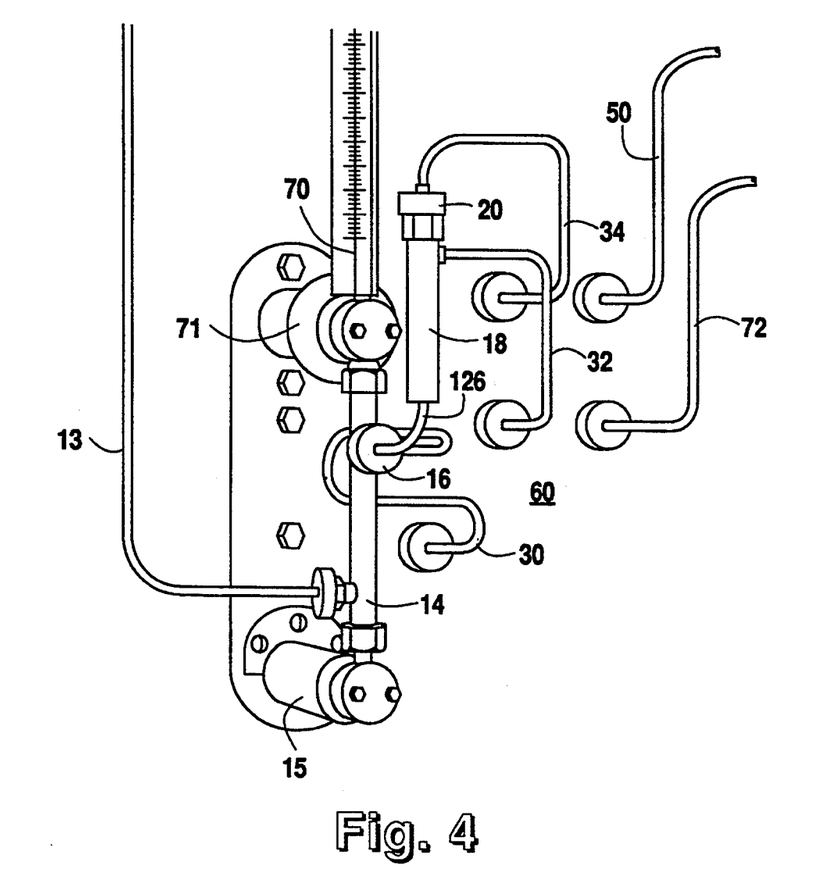
FIG. 4 is a detailed perspective view of the heater section and time reactor of the preferred embodiment of the present invention shown generally in FIG. 2.

Reference is now made to FIG. 4 for a detailed description of heater section 14 and time reactor 18 of the preferred embodiment of the present invention. The main test section of the apparatus of the present invention is comprised primarily of heater section 14 and time reactor 18 in conjunction with filter assemblies 16 and 20 associated with each. Fresh test fluid is conducted to heater section 14 by way of test fluid conduit 13. Test fluid conduit 13 is removably coupled to heater section 14 so that heater section 14 and its ancillary components may be removed for replacement of heater tube 104 (not shown), and for cleaning of the various parts. Heater section 14 itself is connected to the apparatus cabinet by way of lower heater section connector 15 and upper heater section connector 17. These connections 15 and 17 provide the necessary electrical contacts to heater tube 104 (not shown) to allow a current of electricity to flow through heater tube 104, and to raise the temperature of the test fluid within heater section 14 to the necessary level. At an outlet point of heater section 14 is mounted heater section filter assembly 16. The test fluid flows through an interior column within heater section 14, and out through heater section filter assembly 16. As it passes through heater section filter assembly 16, any solids which have formed as a result of oxidation reactions initiated by the heating, will be filtered out. The heating of heater section 14 itself is controlled by a means described in more detail below, and is regulated by measurements received through thermocouple assembly 70. Thermocouple assembly 70 incorporates a thermocouple wire which passes down into heater tube 104 (not shown) from an upper end of heater section 14.

After passing from heater section filter assembly 16, the test fluid flows by way of intermediate conduit 126 into an inlet of time reactor 18. Time reactor 18 is mounted closely adjacent to heater section 14 so that the temperature of the test fluid does not drop significantly from its temperature within heater section 14. One alternative embodiment of the present invention incorporates insulated material around time reactor 18 for the purpose of further reducing the heat losses after the test fluid leaves heater section 14. After passing through time reactor 18, the test fluid passes out through time reactor filter assembly 20 in a process much like that with filter assembly 16 for heater section 14. Both heater section filter assembly 16 and time reactor filter assembly 20 are structured so that the filters and the connecting conduits are easily removable from the system.

Finally, the test fluid leaves time reactor 18 by way of third differential pressure port 34, and flows into cabinet 60 to return back to the front of cabinet 60 by way of spent fluid conduit 72. From spent fluid conduit 72, the test fluid enters water displacement reservoir 22 where it is captured until the test is completed.

A number of additional conduits are shown attached to heater section 14 and time reactor 18, which allow for the measurement of differential pressures across filter assembly 16 and 20. First differential pressure port 30 is a conduit which is connected prior to heater section filter assembly 16, and enters cabinet 60 to be connected to heater section bypass valve 38, and from there to heater section differential pressure transducer 42. A second pressure measuring conduit is connected prior to time reactor filter assembly 20 at time reactor 18, and passes into cabinet 60 by way of second differential pressure port 32. This conduit 32 connects first through absolute pressure transducer 36 (not shown), and then to time reactor bypass valve 40 and heater section bypass valve 38. Connections to transducers 42 and 44 are as described above with regards to FIG. 1. A final pressure is measured by way of third differential pressure port 34, which also serves in FIG. 4 to conduct the test fluid away from time reactor filter assembly 20.

Also shown in FIG. 4 is water reservoir vent conduit 50, which passes into cabinet 60 from water reservoir 22 to be connected to heater section pressure bleed valve 46 (not shown) for the purpose of venting any pressure which collects within water reservoir 22.

In some test situations, it is not necessary to increase the residence time of the test fluid in a heated condition. In such test situations, time reactor 18 may be removed from the system entirely, and a conduit may be connected from heater section filter assembly 16 directly to third differential pressure port 34. This arrangement eliminates not only time reactor 18, but time reactor filter assembly 20, and the necessity of an additional port for the measurement of a second differential pressure. As mentioned above, each of the components described in FIG. 4 are easily removable from the system by means of hand tightened connectors. This easy removal is necessary because the components contain elements which, after the test has been completed, must be visually analyzed for evidence of oxidation deposits.

Figure 5:
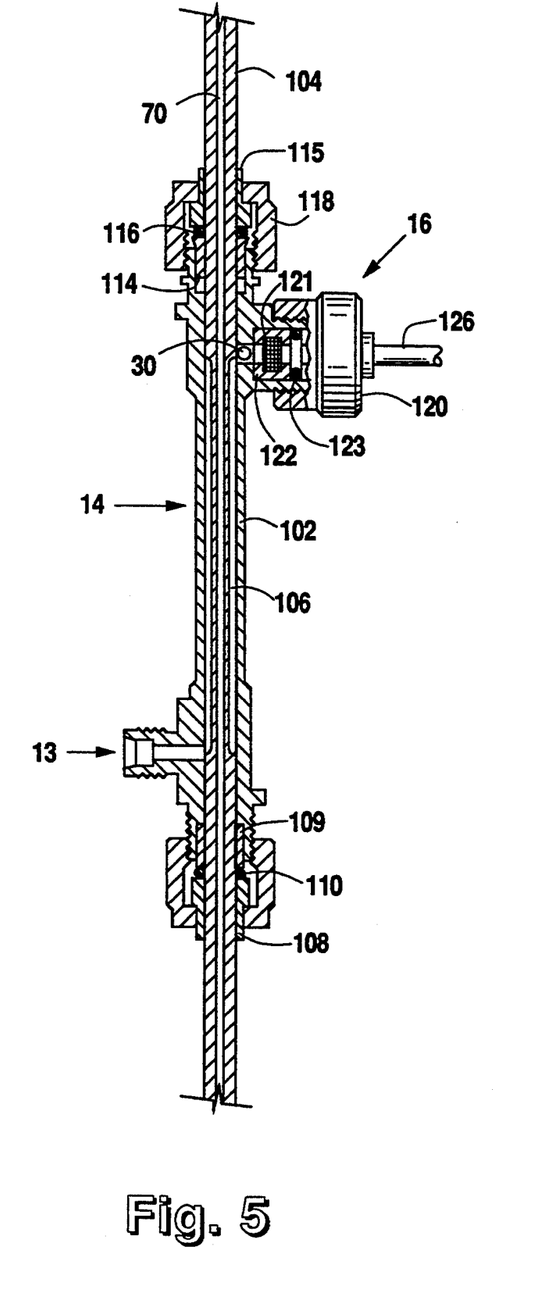
FIG. 5 is a cross sectional view of the heater section of the preferred embodiment of the present invention.

Reference is now made to FIG. 5 for a detailed description of the interior components of heater section 14. Heater section 14 is comprised of heater housing 102 which has a generally cylindrical bore therethrough and is equipped with an inlet from test fluid conduit 13 and an outlet to intermediate fluid conduit 126. Each end of heater housing 102 is equipped with a removable cap 112 and 118, through which is mounted heater tube 104. In the preferred embodiment heater tube 104 has a substantially constant internal diameter, but has an outside diameter that is larger at the extremities than it is in the central portion. Heater tube 104 is electrically insulated from heater housing 102 and removable caps 112 and 118 by means of high dielectric insulators 108, 109, 114, and 115. Ring seals 110 and 116 on each end of heater housing 102 prevent leakage of the test fluid out of heater housing 102 around heater tube 104. Thermocouple 70 is mounted inside heater tube 104 to measure the temperature therein. Thermocouple 70 is positioned to sense and control the maximum temperature of heater tube 104.

As can be seen from FIG. 5, the test fluid upon flowing through test fluid annulus 106 between the internal walls of heater housing 102 and the exterior surface of heater tube 104 passes out of heater housing 102 and through heater section filter assembly 16. At heater section filter assembly 16 is heater filter insert 122. A piece of precision woven stainless steel cloth 121 is held in heater filter insert 122. Heater filter insert 122 and conduit 126 are secured to heater housing 102 by heater filter cap 120. Filter seal 123 is used to seal against leakage. Connection to the pressure differential measuring system is by way of first differential pressure port 30. Should heater filter 121 become clogged, the test fluid may bypass heater filter 121 and flow instead through first differential pressure port 30 as generally described above.

Heater tube 104 is heated by flowing electricity directly therethrough. Fluid cooled heater connectors 15 and 17 (FIG. 4) are attached at each end of heater tube 104 and provide both the electrical current for heating heater tube 104, and the coolant liquid for the purpose of protecting the adjoining components of heating assembly 88 (not shown). This method of heating has several advantages in that it leaves the inside of heater tube 104 open so that its entire length may be probed for temperature measurement. It permits a minimum diameter of ⅛th inch or smaller with very high heat flux, it allows heater tube 104 to be manufactured from any material available in tubing form such as aluminum for lower temperatures and stainless steel or titanium for higher temperatures, and is typically so economical that a new heater tube 104 can be used for each test.

Figure 6:
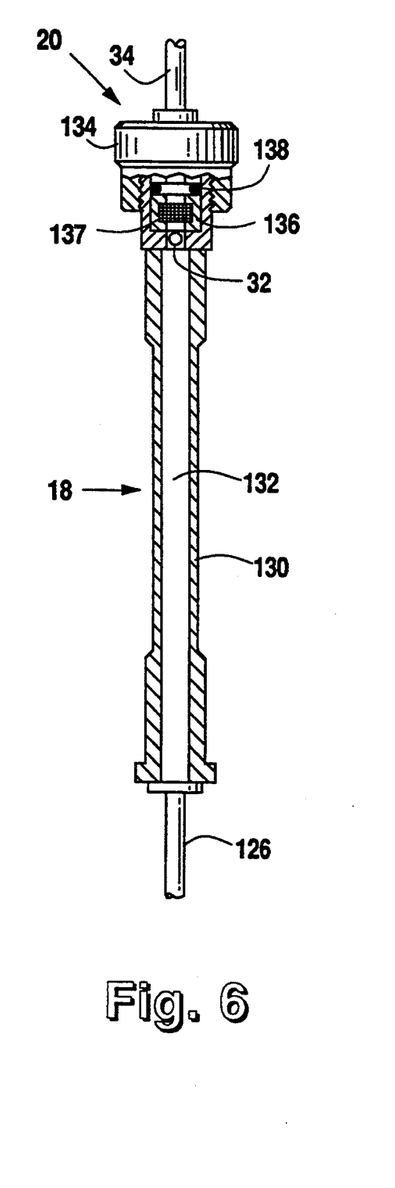
FIG. 6 is a cross sectional view of the time reactor of the preferred embodiment of the present invention.

Reference is now made to FIG. 6 for a detailed description of time reactor 18 shown generally in FIG. 4. After exiting heater section 14 by way of conduit 126, the test fluid enters time reactor 18. Time reactor 18 is comprised of time reactor housing 130 capped at an outlet end by removable cap 134. Ring seal 138 prevents the test fluid from leaking out of time reactor 18. The volume of reactor cylinder 132 of time reactor 18 controls the residence time of the test fluid within time reactor 18. The larger the volume of reactor cylinder 132, the longer the test fluid residence time.

The test fluid exits time reactor 18 by passing through time reactor filter assembly 20 and thence to conduit 34. The reactor filter assembly 20 consists of a piece of precision woven stainless steel cloth 137 held in filter insert 136. Filter insert 136 and conduit 34 are secured to time reactor housing 130 by means of removable cap 134. Ring seal 138 prevents the escape of the test fluid around removable cap 134. Should filter assembly 20 become clogged, the test fluid may bypass filter 137 and instead flow through second differential pressure port 32. Normally the test fluid will continue through conduit 34 to water reservoir 22 as described above with regard to FIG. 1.

Figure 7:
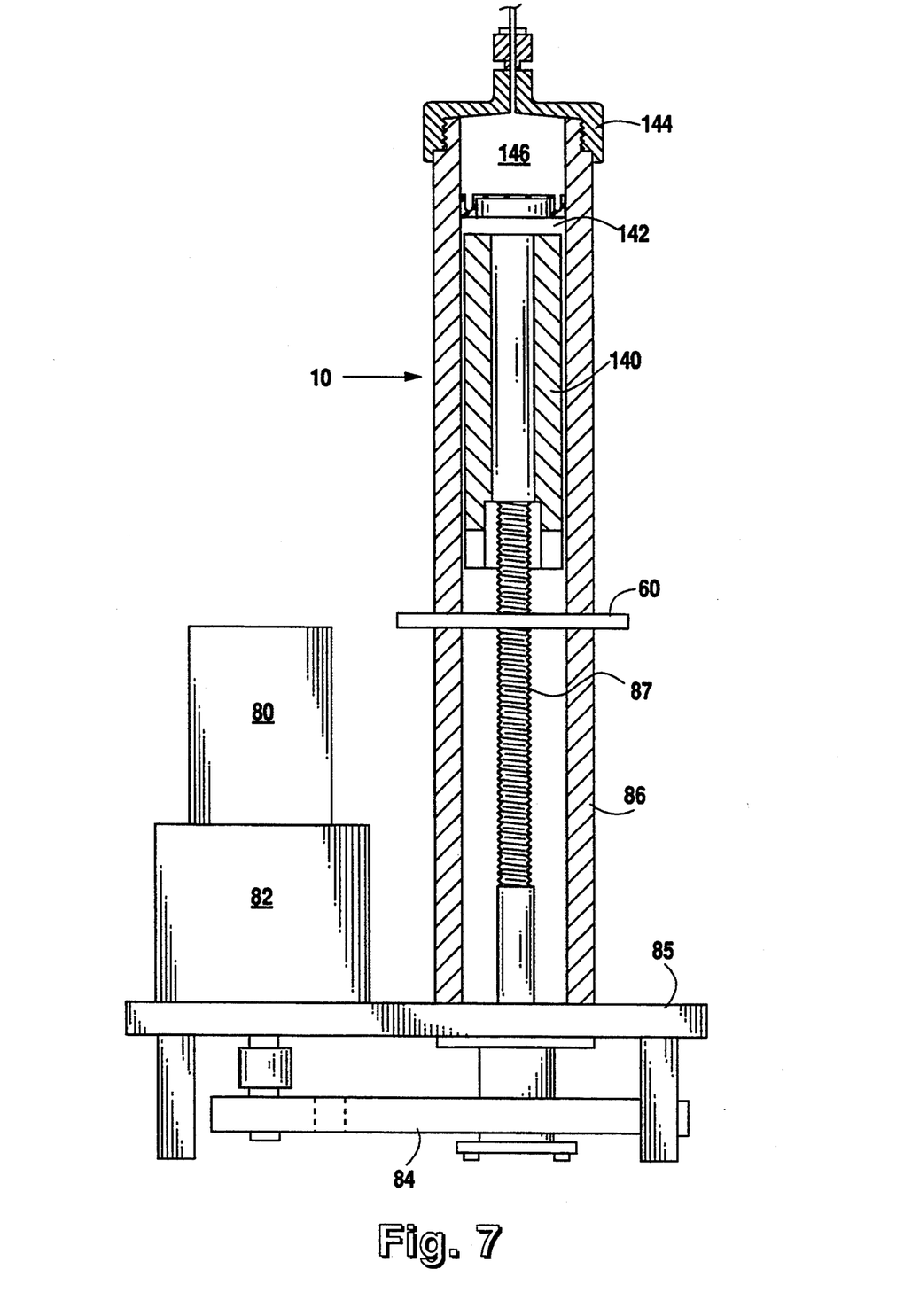
FIG. 7 is a partial cross sectional view of the screw drive assembly and test fluid reservoir of the preferred embodiment of the present invention.

Reference is now made to FIG. 7 for a detailed description of test fluid reservoir 10 and the means for forcing the test fluid into the system by way of drive motor 80. FIG. 7 is a cross sectional view of test fluid reservoir 10, and the associated drive mechanisms which force the test fluid from test fluid reservoir 10. Test fluid is first contained within test fluid cylinder 146 defined by test fluid reservoir 10. Test fluid reservoir 10 is generally a cylindrical structure within which test fluid reservoir piston 140 is able to move freely. At one end of test fluid reservoir 10 is threaded cap 144, which when attached to reservoir 10, makes reservoir 10 substantially air tight, except for the outlet which connects to prefilter 12 (not shown). Piston 144 is sealed against the interior walls of test fluid cylinder 146 by means of sealing gaskets attached to piston head 142, and when moved upward against the test fluid within test fluid cylinder 146, causes test fluid to exit reservoir 10 and enter the test system. Piston 140 is pushed from below by drive screw 87, which is attached through belt 84 to gear reducer 82, and from there to drive motor By this arrangement, piston 140 can be incrementally moved upward to force test fluid from reservoir 10 in graduated amounts. Drive motor 80 is controlled by a reversible DC current that allows the rapid lowering of piston 140 at the end of a test cycle in preparation for a subsequent cycle. Test fluid reservoir 10 is mounted on the exterior of cabinet 60, and connects through the wall of cabinet 60 to drive screw assembly 86 and drive unit stand 85. The electrical and electronic connections which provide power to drive motor 80 and which control its speed, pass through the system controller (not shown), and function in conjunction with the data acquisition of the system (not shown) so as to closely regulate the flow of the test fluid into the test system at its initial point.

ALTERNATIVE RETROFIT EMBODIMENT

Since the present invention is primarily an improvement upon an earlier design for a similar test apparatus, it would be advantageous for the improved elements of the present invention to be capable of incorporation into the apparatus of the earlier design. It is, therefore, possible to easily implement the unique features of the present invention in conjunction with the basic test system of the earlier Hundere patent described above, so as to eliminate the need to completely replace the test apparatus in order to enjoy the advantages of the present invention.

A stand alone unit which incorporates the appropriate control and data acquisition elements, and further utilizes the improved screw drive test fluid reservoir system described above in connection with FIG. 7, can be easily retrofitted onto earlier designs of the Hundere fuel testing apparatus. Time reactor 18 and time reactor filter assembly 20 may be easily connected in a series with heater section elements of earlier designs, and thereby appropriately increase the residence time of the test fluid undergoing analysis. Test fluid reservoir 10 and drive screw assembly 86 may replace the inline metering pump present in the earlier designs, and thereby alter the flow system of the earlier design from a circuitous flow to an inlet/outlet, straight line flow. Once the circuitous flow of the earlier design is broken, the water displacement reservoir system of the present invention can be easily incorporated into the outlet of the time reactor assembly that has been added. The heater section elements of the earlier design, in conjunction with the pressure monitoring elements of the earlier apparatus, may be retained and supplemented by the fluid reservoir system of the present invention, as well as the water displacement system and the additional pressure measuring systems.

Reference is now made again to FIG. 1 and FIG. 2 for a detailed description of the sequence of steps appropriate to implement the method of the preferred embodiment of the present invention. In the preferred embodiment, these steps are primarily performed in automated sequential fashion by the combination of a digital system controller and a data acquisition system.

To a great extent, operator intervention is not necessary once the test has been set up, and the system has been started. The operator is primarily required for the system setup, the system reset, and the re-calibration steps that must occur prior to and after the running of a test.

Preparation for running a test includes aeration of the test fluid using a flow of air provided by aeration pump 98 (FIG. 3) by way of aeration port 64 (FIG. 2). The air flow may be controlled and regulated by air flow regulator 66. A volume of air must be dissolved within the test fluid prior to the test being run, so that an adequate level of thermal oxidation may occur. In the real world, this aeration of the fuel or fluid may occur at any number of points in a vehicle's engine system. The aeration, therefore, is intended to provide the same degree of dissolved oxygen within the fluid that by experimental analysis could be expected to occur in engines utilizing such fuels.

Once aerated, the test fluid is placed within the test fluid reservoir 10. This is accomplished by the removal of cylinder cap 144 (FIG. 7) and the placement of the test fluid within fluid cylinder 146. Cylinder cap 144 is then replaced on test fuel reservoir 10.

A number of additional preliminary steps must be taken to prepare the system for the test run. Each of the differential pressure transducers 42 and 44 must be zeroed out so that any remaining pressure in the system showing on the transducers is negated. Likewise, absolute pressure transducer 36 must have been previously calibrated and zeroed in preparation for the test run. Water reservoir 22 must have a sufficient amount of displaceable water within in it to be replaced by the amount of test fluid expected to pass through the system. Pressure regulator 24 should be preset to allow a flow of water that will maintain a sufficient back pressure on the system that will keep the test fluid from vaporizing at the temperatures expected to be created by heater section 14.

Finally, the conditions of bypass valves 38 and 40 should be preset so that they properly conduct the appropriate pressures to differential pressure transducers 42 and 44. Heater section filter assembly 16 and time reactor filter assembly 20 should, of course, have been cleaned and/or replaced after the previous test was completed. Additionally, heater tube 104 in the previous test should be replaced with a new, deposit free heater tube. All seals should be checked, and the system should be prepared to initiate the automated test sequence.

Initiating the automated test sequence starts drive motor 80, which by way of gear reducer 82, turns drive screw 87 which forces piston 140 upwards through fluid cylinder 146. This action displaces the test fluid from fluid cylinder 146 at a controlled rate. Starting the test sequence also starts the flow of electricity through heating assembly 88 and the coolant flow associated therewith.

The test fluid passes out of test fluid reservoir 10, through prefilter 12, into heater section 14. Prefilter 12 serves to initially strain the test fluid of particulate matter that might damage the test system or prevent an accurate measurement of heat related deposits. Within heater section 14, the test fluid is raised to a predetermined temperature selected by the test operator or controlled by the automated test sequence. The temperature is monitored by thermocouple 70, and is correspondingly regulated through heater assembly 88.

From heater section 14, the test fluid passes out through heater section filter assembly 16 into time reactor 18. At this point, it is expected that some deposits have already started to occur, both on heater tube 104 and suspended within the test fluid. Those that are formed on heater tube 104 will remain until after the test is complete, for visual examination, and those that are collected by heater section filter assembly 16 may both be examined after the test is completed, and indirectly measured during the test by the differential pressure across heater section filter assembly 16.

If the test requires additional residence time, time reactor 18 may be included in the circuit after heater section 14, as indicated in the figures. It is possible that additional residence time will not always be necessary for a given test, and time reactor 18 may be left out of the system altogether. In such a case, test fluid passes out of heater section 14 through heater section filter 16 directly into water reservoir 22. Pressure measurements in this alternate configuration may still be obtained by connecting a conduit (not shown) from heater section filter assembly 16 directly to pressure differential port 34. Appropriate orientation of bypass valve 40 and bypass valve 38 then allow heater section differential pressure transducer 42 to keep track of the differential pressure across heater section filter 16. This configuration also takes differential pressure transducer 44 out of the system circuit. Absolute pressure transducer 36 remains in the circuit.

With time reactor 18 in the circuit, the test fluid remains for a somewhat longer period of time at the elevated temperature provided by heater section 14. This additional residence time in a heated state increases the amount of deposits that form prior to time reactor filter assembly 20. Time reactor 18, in conjunction with time reactor filter assembly 20, therefore, provides an additional point at which quantitative measurements of oxidation deposits can be made. As with heater section filter assembly 16, the differential pressure across time reactor filter 20 can be measured and correlated to a level of deposits while the test is running.

From time reactor 18, the test fluid passes on into water reservoir 22. Within water reservoir 22, the test fluid displaces an equal volume of water out through water conduit 74. Within water reservoir 22, test fluid remains on the top surface of the initial amount of water present, and gradually forces the water from water reservoir 22 by way of pressure regulator 24. As mentioned above, the setting of pressure regulator 24 maintains a back pressure on the water within water reservoir 22, and therefore a back pressure on the test fluid as it passes into water reservoir 22. This maintains a constant background pressure on the entire test system, wherein the test fluid is being heated. This back pressure prevents vaporization of the test fluid at elevated temperatures, and ensures more accurate quantitative and qualitative measurements of the deposition characteristics.

After passing through pressure regulator 24, the water from water reservoir 22 finally passes out into effluent reservoir 26. Since no toxic or volatile test fluid escapes from the test system during the operation of the test, operator attention to the process is minimized. The water as effluent may be easily disposed of, and a more careful disposal or recycling of the test fluid, once the test is complete, may be later accomplished as described below by removal of the test fluid from water reservoir 22.

Concurrent with the flow of test fluid through the system as described above, the system controller and data acquisition units maintain a constant quantitative determination of the changes in the system pressure at various points throughout. These pressures are measured prior to and after each of the filters 16 and 20. When only heater section 14 is incorporated into the test flow system, only two points of pressure are collected and analyzed as described above. When time reactor 18 is additionally included within the system, pressure is monitored at three points so as to determine differential pressures across each of the two filters 16 and 20. A first pressure value is obtained by way of pressure differential port 30, which is between heater section 14 and heater section filter assembly 16. This pressure is conducted to heater section differential pressure transducer 42 by way of heater section bypass valve 38. A second pressure to be compared with this first pressure is provided to heater section differential pressure transducer 42 by way of heater section bypass valve 38 and by way of absolute pressure transducer 36. The second pressure is obtained from a point prior to time reactor filter assembly 20 by way of pressure differential port 32. Heater section differential pressure transducer 42, therefore, provides the system controller and data acquisition units, and the operator via display 63, a constant quantitative measurement of the pressure drop across heater section filter assembly 16, and therefore, an indication of the amount of deposits that are forming on heater section filter assembly 16.

A similar differential pressure measurement is made across time reactor filter assembly 20 by way of time reactor bypass valve 40 and time reactor differential pressure transducer 44. A first pressure is obtained by way of absolute pressure transducer 36 from pressure differential port 32 through time reactor bypass valve 40 to one side of time reactor differential pressure transducer 44. A second pressure is obtained after time reactor filter assembly 20 by way of pressure differential port 34 through time reactor bypass valve 40 to a second side of time reactor differential pressure transducer 44. The quantitative measurements based upon this differential pressure across time reactor filter assembly 20 are provided to the system controller and data acquisition device, and to the test operator as described above.

To summarize the quantitative measurements that are made with the method of the preferred embodiment of the present invention, it can be seen that direct measurements of deposits by post test visual examination of heater tube 104, heater section filter assembly 16, and time reactor filter assembly 20, may be made in combination with indirect measurements of these deposits on a real time basis by way of differential pressure measurements obtained through differential pressure transducers 42 and 44.

In addition to the analytical functions that the differential pressure devices serve, a certain level of safety is maintained by the constant monitoring of the pressure within the test system. If for whatever reason some element of the system became clogged with deposits and the pressure exceeded a level suitable for the system, the absolute pressure transducer 36 would signal the system controller to terminate the test, and notify the test operator of the problem. Likewise, if there were a sudden drop in the pressure within the system prior to the termination of the test that would be indicative of a leak within the system, the absolute pressure transducer 36 could terminate the flow of test fluid and notify the test operator by way of display 63. In any of these situations, bypass valves 38 and 40 are capable of rerouting the test fluid around the filters, by simply redirecting the flow through the conduits that normally serve to measure the differential pressures. When switched, bypass valves 38 and 40 could conduct the test fluid through differential pressure port 30, through bypass valve 38, into bypass valve 40, and back through differential pressure port 34 directly into water reservoir 22.

Once the system has run a test, a number of vent and bleed operations must occur before the system components may be opened to expose the deposits that have formed. These vent and bleed operations are primarily performed by heater section differential pressure bleed valve 46 and time reactor differential pressure bleed valve 48. By way of heater section bleed valve 46, the pressures built up on heater section differential pressure transducer 42 are released by way of accumulator 52, through air trap 54, check valve 56, and finally by way of effluent conduit 58 into effluent reservoir 26. Likewise, the differential pressures that have been built up across time reactor differential pressure transducer 44 are released by way of time reactor bleed valve 48 through the same series of components finally into effluent reservoir 26. Residual pressure that remains in water reservoir 22, due to the back pressure caused by a pressure regulator 24, is released through heater section differential pressure bleed valve 46 through the same series of elements as described above. This allows every part of the system to depressurize and reset to a condition that is both favorable for removable of those parts of the system that retain deposits for examination, and for the restart of the system for a subsequent test.

In addition to the real time measurements made on the deposits formed on filter assemblies 16 and 20, post test measurements of the deposits can be made by removal of heater tube 104 from heater housing 102, and a visual examination of the condition of the surface of heater tube 104. Likewise, heater filter insert 122, which contains heater filter 121, as well as time reactor filter insert 136, which contains time reactor filter 137, may be removed from heater section filter assembly 16 and time reactor filter assembly 20, so that a visual analysis may be made of the deposits that have formed therein. These visual measurements, in conjunction with the differential pressure measurements and the time over which these differential pressure measurements vary, provide the necessary quantitative and qualitative information for the test apparatus to accurately indicate the thermal oxidation characteristics of the tested fluid.

While the invention has been described in connection with a preferred embodiment and a number of alternative preferred embodiments, it is not intended to limit the invention to the particular forms or practices set forth, but, on the contrary, it is intended to cover such further alternatives, modifications, and equivalences as may be included within the spirit and scope of the invention and the claims.

I claim:

1. An apparatus for retrofitting to a device for testing thermal oxidation stability of a fluid, such as a hydrocarbon fuel, which device utilizes a circuitous fluid flow system and a means for heating said fluid, said apparatus comprising:

a non-circuitous fluid flow conduit system with an input and an output, said conduit system capable of conducting and containing said fluid;

means for inserting an amount of said fluid into said conduit system at said input of said conduit system;

means for creating and maintaining an incremental flow of said fluid through said conduit system, said incremental flow being maintained at a regulated pressure and being from said input towards said output of said conduit system; and means for increasing a total residence time of said fluid within said conduit system at a location between said heating means and said output of said conduit system.

2. A method of testing thermal oxidation stability of a fluid such as a hydrocarbon fuel, comprising the steps of:

retrofitting a device for testing thermal oxidation stability of a fluid, such as a hydrocarbon fuel, which device utilizes a circuitous fluid flow system and a means for heating said fluid;

storing said fluid in a closed reservoir having a movable piston therein, said piston capable of forcing said fluid from said reservoir as said piston moves from a first end of said reservoir to a second end of said reservoir, said reservoir having an outlet at said second end;

controllably discharging said fluid from said reservoir by moving said piston from said first end of said reservoir to said second end of said reservoir;

conducting said fluid from said outlet of said reservoir to said means for heating said fluid;

conducting said fluid through said means for heating said fluid;

controllably heating said fluid while in said heating means, thereby forming suspended solids from said fluid;

filtering said fluid of said suspended solids formed as a result of said heating by passing said fluid through a first filter located at an outlet of said heating means;

measuring a differential pressure across said first filter and correlating said differential pressure with a degree of accumulation of said suspended solids on said filter;

conducting said fluid to a spent fluid reservoir containing water, said water capable of being displaced from said spent fluid reservoir by said fluid upon entering said spent fluid reservoir, said spent fluid reservoir having an inlet and an outlet;

displacing said water from said spent fluid reservoir with said fluid by forcing said water from said spent fluid reservoir by way of said outlet;

conducting said water through a pressure regulator valve designed to regulate outflow of said water from said spent fluid reservoir in a manner which maintains constant pressure within said apparatus;

removing said first filter from said outlet of said heating means and examining said first filter for deposits of said suspended solids thereon; and removing said spent fluid from said spent fluid reservoir and examining said spent fluid reservoir for deposits of said suspended solids therein.

3. An apparatus for testing thermal oxidation stability of a fluid such as a hydrocarbon fuel, comprising:

a non-circuitous fluid flow conduit system with an input and an output, said conduit system capable of conducting and containing said fluid;

means for inserting an amount of said fluid into said conduit system at said input of said conduit system;

means for creating and maintaining an incremental flow of said fluid through said conduit system, said incremental flow being maintained at a regulated pressure and being from said input towards said output of said conduit system;

means for controllably heating said fluid in at least one location within said conduit system, said heating means having a surface in contact with said fluid upon which may be deposited suspended solids formed by said heating of said fluid;

means for increasing a total residence time of said fluid within said conduit system at a location between said heating means and said output of said conduit system;

filter means in at least one location within said conduit system between said heating means and said output of said conduit system for trapping said suspended solids formed by said heating of said fluid;

pressure differential measuring means located in conjunction with said filter means for determining a differential pressure across said filter means, said differential pressure being indicative of a degree of said suspended solids deposited on said filter means; and said filter means and said surface of said heating means being so situated within said conduit system as to be monitored for a build up of said suspended solids thereon, said build up of said suspended solids being indicative of said thermal oxidative stability of said fluid, wherein said means for creating and maintaining an incremental flow of said fluid through said conduit system, said means for controllably heating said fluid, and said pressure differential measuring means, are all automatically controlled and monitored by a microprocessor based control and data acquisition system.

4. The apparatus claimed in claim 3, wherein said means for creating and maintaining an incremental flow of said fluid through said conduit system comprises:

a fresh flow reservoir located at said input of said conduit system, said fresh fluid reservoir having a movable piston therein, said movable piston serving to force said fluid from said fresh fluid reservoir as said piston moves from a first end of said fresh fluid reservoir to an outlet at a second end of said fresh fluid reservoir;

a spent fluid reservoir located at said output of said conduit system, said spent fluid reservoir containing water, said water capable of being displaced from said spent fluid reservoir by said fluid flowing into said spent fluid reservoir, said spent fluid reservoir having an inlet and an outlet; and a pressure regulator valve located at said outlet of said spent fluid reservoir, said pressure regulator valve designed to regulate said displacement of said water from said spent fluid reservoir in a manner which maintains a constant pressure within said apparatus.

5. The apparatus claimed in claim 3, wherein said means for increasing a total residence time of said fluid within said conduit system comprises a time reactor housing having an inlet and an outlet for flowing said fluid therethrough, said time reactor housing having an interior chamber of a size sufficient to reduce said incremental flow of said fluid therethrough.

6. The apparatus claimed in claim 3, wherein at least one of said filter means comprises a precision wire screen placed downstream and proximate to said means for controllably heating said fluid.

7. The apparatus claimed in claim 3, wherein at least one of said filter means comprises a precision wire screen placed downstream and proximate to said means for increasing a total residence time of said fluid within said conduit system.

8. The apparatus claimed in claim 3, wherein said pressure differential measuring means comprises:
first pressure measuring means located upstream and proximate to said filter means;
second pressure measuring means located downstream and proximate to said filter means; and
means for comparing a pressure measured by said first pressure measuring means with a pressure measured by said second pressure measuring means.

9. A method of testing the thermal oxidation stability of a fluid such as a hydrocarbon fuel, comprising the steps of:
inserting an amount of said fluid into a non-circuitous fluid flow conduit system with an input and an output, said fluid being inserted at said input of said conduit system;
creating and maintaining an incremental flow of said fluid through said conduit system, said incremental flow being maintained at a regulated pressure and being from said input towards said output of said conduit system;
controllably heating said fluid in at least one location within said conduit system, said heating occurring at a surface in contact with said fluid upon which may be deposited suspended solids formed by said heating of said fluid;
increasing a total residence time of said fluid within said conduit system at a location between said location at which said heating occurs and said output of said conduit system;
filtering said fluid in at least one location within said conduit system between said location at which said heating occurs and said output of said conduit system thereby trapping said suspended solids formed by said heating of said fluid;
measuring a differential pressure across said location at which said filtering occurs, said differential pressure being indicative of a degree of said suspended solids deposited from said filtering; and
monitoring said differential pressure, said surface at which said heating occurs, and said location at which said filtering occurs, for a build up of said suspended solids thereon, said build up of said suspended solids being indicative of said thermal oxidative stability of said fluid,
wherein said steps of creating and maintaining an incremental flow of said fluid through said conduit system, controllably heating said fluid, measuring a differential pressure across said location at which said filtering occurs, and monitoring said differential pressure, are all achieved automatically by way of microprocessor based control and data acquisition system.

10. An apparatus for testing thermal oxidation stability of a fluid such as a hydrocarbon fuel, comprising:
a closed reservoir having a movable piston therein, said piston serving to force said fluid from said reservoir as said piston moves from a first end of said reservoir to a second end of said reservoir, said reservoir having an outlet at said second end;
a heater tube housing having an inlet and an outlet for flowing said fluid therethrough;
a first conduit means connecting said outlet of said reservoir with said inlet of said heater tube housing;
a metallic tubular member removably mounted in said heater tube housing with an exterior surface such that said fluid flowing through said heater tube housing passes over said exterior surface of said tubular member, said tubular member having a substantially constant internal diameter, said tubular member further having an outside diameter larger at an upper and a lower extremity than in a central portion thereof;
means for electrically insulating said tubular member from said heater tube housing;
means for heating said tubular member by passage of electric current therethrough thereby heating said fluid flowing through said heater tube housing and causing said fluid to partially breakdown chemically, resulting in the formation of suspended solids from said fluid;
temperature sensing means mounted inside said tubular member;
first filter means located within said outlet of said heater tube housing for trapping said suspended solids formed by said heating of said fluid in said heater tube housing;
a spent fluid reservoir containing water, said water capable of being displaced from said spent fluid reservoir by said fluid upon entering said spent fluid reservoir, said spent fluid reservoir having an inlet and an outlet;
second conduit means connecting said outlet of said heater tube housing to said inlet of said spent fluid reservoir;
a pressure regulator valve designed to regulate outflow of said water from said spent fluid reservoir in a manner which maintains a constant pressure within said apparatus; and
third conduit means connecting said outlet of said spent fluid reservoir with said pressure regulator valve,
wherein said movable piston within said closed reservoir, said means for heating said tubular member, and said temperature sensing means, are all automatically controlled and monitored by a microprocessor based control and data acquisition system.

11. The apparatus claimed in claim 10, further comprising:
a time reactor housing insertable between said heater tube housing and said spent fluid reservoir, said time reactor housing having an inlet and an outlet for flowing said fluid therethrough, said time reactor housing having an interior chamber of a size sufficient to reduce a flow rate of said fluid therethrough; and
second filter means located at said outlet of said time reactor housing for trapping said suspended solids formed from said fluid in said time reactor housing.

12. The apparatus claimed in claim 10, further comprising first differential pressure measuring means located at said outlet of said heater tube housing and across said first filter means so as to measure a pressure drop across said first filter means and thereby indicate a degree of said suspended solids built up on said first filter means, wherein said first differential pressure measuring means is automatically controlled and monitored by a microprocessor based control and data acquisition system.

13. The apparatus claimed in claim 10, further comprising;
first differential pressure measuring means located at said outlet of said heater tube housing and across said first filter means so as to measure a pressure drop across said first filter means and thereby indicate a degree of said suspended solids built up on said first filter means; and
second differential pressure measuring means located at said outlet of said time reactor housing and across said second filter means so as to measure a pressure drop across said second filter means and thereby indicate a degree of said suspended solids built up on said second filter means,
wherein said first differential pressure measuring means and said second differential pressure measuring means are automatically controlled and monitored by a microprocessor based control and data acquisition system.

14. An apparatus for testing thermal oxidation stability of a fluid such as a hydrocarbon fuel, comprising:
a closed reservoir having a movable piston therein, said piston serving to force said fluid from said reservoir as said piston moves from a first end of said reservoir to a second end of said reservoir, said reservoir having an outlet at said second end;
a heater tube housing having an inlet and an outlet for flowing said fluid therethrough;
first conduit means connecting said outlet of said reservoir with said inlet of said heater tube housing;
a metallic tubular member removably mounted in said heater tube housing with an exterior surface such that said fluid flowing through said heater tube housing passes over said exterior surface of said tubular member, said tubular member having a substantially constant internal diameter, said tubular further having an outside diameter larger at an upper and at a lower extremity than in a central portion thereof;
means for electrically insulating said tubular member from said heater tube housing;
means for heating said tubular member by passage of electric current therethrough and thereby heating said fluid flowing through said heater tube housing and causing said fluid to partially breakdown chemically, resulting in the formation of suspended solids from said fluid;
temperature sensing means mounted inside said tubular member;
first filter means located at said outlet of said heater tube housing for trapping said suspended solids formed by said heating of said fluid in said heater tube housing;
first differential pressure measuring means located at said outlet of said heater tube housing and across said first filter means so as to measure a pressure drop across said first filter means and thereby indicate a degree of said suspended solids built up on said first filter means; p1 a time reactor housing having an inlet and an outlet for flowing said fluid therethrough, said time reactor housing having an interior chamber of a size sufficient to reduce a flow rate of said fluid therethrough;
second conduit means connecting said outlet of said heater tube housing with said inlet of said time reactor housing;
second filter means located within said outlet of said time reactor housing for trapping said suspended solids formed from said fluid in said time reactor housing;
second differential pressure measuring means located at said outlet of said time reactor housing and across said second filter means so as to measure a pressure drop across said second filter means and thereby indicate a degree of said suspended solids built up on said second filter means;
a spent fluid reservoir containing water, said water capable of being displaced from said spent fluid reservoir by said fluid upon entering said spent fluid reservoir, said spent fluid reservoir having an inlet and an outlet;
third conduit means connecting said outlet of said time reactor having to said inlet of said spent fluid reservoir;
a pressure regulator valve designed to regulate outflow of said water from said spent fluid reservoir in a manner which maintains a constant pressure within said apparatus, and
fourth conduit means connecting said outlet of said spent fluid reservoir with said pressure regulator valve,
wherein said movable piston within said closed reservoir, said means for heating said tubular member, said temperature sensing means, said first differential pressure measuring means, and said second differential pressure measuring means, are all automatically controlled and monitored by a microprocessor based control and data acquisition system.

15. A method of testing thermal oxidation stability of a fluid such as a hydrocarbon fuel, comprising the steps of:
storing said fluid in a closed reservoir having a movable piston therein, said piston capable of forcing said fluid from said reservoir as said piston moves from a first end of said reservoir to a second end of said reservoir, said reservoir having an outlet at said second end;
controllably discharging said fluid from said reservoir by moving said piston from said first end of said reservoir to said second end of said reservoir;
conducting said fluid from said outlet of said reservoir to a heater tube housing, said heater tube housing having an inlet and an outlet for flowing said fluid therethrough, said heater tube housing having a metallic tubular member removably mounted therein with an exterior surface, said tubular member having a substantially constant internal diameter, said tubular member further having an outside diameter larger at an upper and a lower extremity than in a central portion thereof; conducting said fluid through said heater tube housing thereby placing said fluid in contact with said exterior surface of said metallic tubular member;
controllably heating said fluid by heating said metallic tubular member while in contact with said fluid, thereby forming suspended solids from said fluid;
filtering said fluid of said suspended solids formed as a result of said heating by passing said fluid through a first filter located at said outlet of said heater tube housing;

measuring a differential pressure across said first filter and correlating said differential pressure with a degree of accumulation of said suspended solids on said filter;

conducting said fluid to a spent fluid reservoir containing water, said water capable of being displaced from said spent fluid reservoir by said fluid upon entering said spent fluid reservoir, said spent fluid reservoir having an inlet and an outlet;

displacing said water from said spent fluid reservoir with said fluid by forcing said water from said spent fluid reservoir by way of said outlet;

conducting said water through a pressure regulator valve designed to regulate outflow of said water from said spent fluid reservoir in a manner which maintains constant pressure within said apparatus;

removing said metallic tubular member from said heater tube housing an examining said metallic tubular member for changes in appearance indicative of deposits of said suspended solids thereon;

removing said first filter from said outlet of said heater tube housing and examining said first filter for deposits of said suspended solids thereon; and removing said spent fluid from said spent fluid reservoir and examining said spent fluid reservoir for deposits of said suspended solids therein, wherein said steps of controllably discharging said fluid, controllably heating said fluid, measuring a differential pressure across said first filter, and correlating said differential pressure, are all achieved automatically by way of a microprocessor based control and data acquisition system.

16. The method claimed in claim 15, further comprising the steps of:

conducting said fluid from said heater tube housing to a time reactor housing prior to said step of conducting said fluid to said spent fluid reservoir, said time reactor housing having an inlet and an outlet for flowing said fluid therethrough, said time reactor housing having an interior chamber of a size sufficient to reduce the flow rate of said fluid therethrough;

filtering a second time said fluid of any suspended solids formed as a result of said heating by passing said fluid through a second filter located at said outlet of said time reactor housing;

measuring a second differential pressure across said second filter and correlating said second differential pressure with a degree of accumulation of said suspended solids on said second filter; and removing said second filter from said outlet of said time reactor housing after said step of conducting said fluid to said spent fluid reservoir, and examining said second filter for deposits of said suspended solids thereon, wherein said steps of controllably discharging said fluid, controllably heating said fluid, measuring a differential pressure across said first filter, correlating said differential pressure, measuring a second differential pressure across said second filter, and correlating said second differential pressure, are all achieved automatically by way of a microprocessor based control and data acquisition system.

* * * * *